(12) United States Patent
Czernik et al.

(10) Patent No.: US 10,863,992 B2
(45) Date of Patent: Dec. 15, 2020

(54) ENDOSCOPIC SURGICAL CLIP APPLIER

(71) Applicant: Covidien LP, Mansfield, MA (US)

(72) Inventors: Roman Czernik, Trumbull, CT (US); Brian J. Creston, West Haven, CT (US); Jacob C. Baril, White Plains, NY (US); Thomas A. Zammataro, Hamden, CT (US)

(73) Assignee: Covidien LP, Mansfield, MA (US)

( * ) Notice: Subject to any disclaimer, the term of this patent is extended or adjusted under 35 U.S.C. 154(b) by 351 days.

(21) Appl. No.: 16/030,926

(22) Filed: Jul. 10, 2018

(65) Prior Publication Data

US 2019/0046207 A1    Feb. 14, 2019

Related U.S. Application Data

(60) Provisional application No. 62/542,325, filed on Aug. 8, 2017.

(51) Int. Cl.
*A61B 17/128* (2006.01)
*A61B 34/35* (2016.01)
(Continued)

(52) U.S. Cl.
CPC .......... *A61B 17/1285* (2013.01); *A61B 34/35* (2016.02); *A61B 34/37* (2016.02);
(Continued)

(58) Field of Classification Search
CPC ...... A61B 17/1285; A61B 2017/00367; A61B 2017/0046; A61B 2017/00477;
(Continued)

(56) References Cited

U.S. PATENT DOCUMENTS 3,120,230 A    2/1964  Skold
3,638,847 A    2/1972  Noiles et al.
(Continued)

FOREIGN PATENT DOCUMENTS

AU    2013254887 A1    11/2013
CA       1163889 A      3/1984
(Continued)

OTHER PUBLICATIONS

International Search Report corresponding to Int'l Patent Appln. PCT/US2018/050316 dated Dec. 31, 2018.
(Continued)

*Primary Examiner* — George J Ulsh
*Assistant Examiner* — Andrew P. Restaino
(74) *Attorney, Agent, or Firm* — Carter, DeLuca & Farrell LLP

(57) ABSTRACT

A shaft assembly of an apparatus for applying surgical clips to body tissue includes an elongated spindle, a trip block reciprocally supported on a proximal portion of the spindle, a biasing member extending between the proximal portion of the spindle and the trip block, and a pusher bar having a proximal portion fixedly coupled to the trip block. The pusher bar has a distal portion configured to load a distal-most surgical clip into a pair of jaws during distal movement of the trip block, via distal movement of the spindle, and remain in a distally advanced position during an approximation of the pair of jaws.

19 Claims, 8 Drawing Sheets

(51) Int. Cl.
*A61B 17/00* (2006.01)
*A61B 90/00* (2016.01)
*A61B 34/37* (2016.01)
*A61B 34/30* (2016.01)

(52) U.S. Cl.
CPC .......... *A61B 2017/0046* (2013.01); *A61B 2017/00367* (2013.01); *A61B 2017/00477* (2013.01); *A61B 2034/301* (2016.02); *A61B 2090/034* (2016.02)

(58) Field of Classification Search
CPC ........ A61B 2034/301; A61B 2090/034; A61B 34/35; A61B 34/37
See application file for complete search history.

(56) References Cited

U.S. PATENT DOCUMENTS

| | | | |
|---|---|---|---|
| 3,735,762 | A | 5/1973 | Bryan et al. |
| 4,226,242 | A | 10/1980 | Jarvik |
| 4,242,902 | A | 1/1981 | Green |
| 4,296,751 | A | 10/1981 | Blake, III et al. |
| 4,372,316 | A | 2/1983 | Blake, III et al. |
| 4,408,603 | A | 10/1983 | Blake, III et al. |
| 4,418,694 | A | 12/1983 | Beroff et al. |
| 4,471,780 | A | 9/1984 | Menges et al. |
| 4,480,640 | A | 11/1984 | Becht |
| 4,480,641 | A | 11/1984 | Failla et al. |
| 4,487,204 | A | 12/1984 | Hrouda |
| 4,487,205 | A | 12/1984 | Di Giovanni et al. |
| 4,491,133 | A | 1/1985 | Menges et al. |
| 4,492,232 | A | 1/1985 | Green |
| 4,498,476 | A | 2/1985 | Cerwin et al. |
| 4,500,024 | A | 2/1985 | DiGiovanni et al. |
| 4,509,518 | A | 4/1985 | McGarry et al. |
| 4,512,345 | A | 4/1985 | Green |
| 4,522,207 | A | 6/1985 | Klieman et al. |
| 4,532,925 | A | 8/1985 | Blake, III |
| 4,534,351 | A | 8/1985 | Rothfuss et al. |
| 4,545,377 | A | 10/1985 | Cerwin et al. |
| 4,549,544 | A | 10/1985 | Favaron |
| 4,556,058 | A | 12/1985 | Green |
| 4,557,263 | A | 12/1985 | Green |
| 4,562,839 | A | 1/1986 | Blake, III et al. |
| 4,572,183 | A | 2/1986 | Juska |
| 4,576,165 | A | 3/1986 | Green et al. |
| 4,576,166 | A | 3/1986 | Montgomery et al. |
| 4,590,937 | A | 5/1986 | Deniega |
| 4,598,711 | A | 7/1986 | Deniega |
| 4,602,631 | A | 7/1986 | Funatsu |
| 4,611,595 | A | 9/1986 | Klieman et al. |
| 4,612,932 | A | 9/1986 | Caspar et al. |
| 4,616,650 | A | 10/1986 | Green et al. |
| 4,616,651 | A | 10/1986 | Golden |
| 4,624,254 | A | 11/1986 | McGarry et al. |
| 4,637,395 | A | 1/1987 | Caspar et al. |
| 4,646,740 | A | 3/1987 | Peters et al. |
| 4,647,504 | A | 3/1987 | Kimimura et al. |
| 4,658,822 | A | 4/1987 | Kees, Jr. |
| 4,660,558 | A | 4/1987 | Kees, Jr. |
| 4,662,373 | A | 5/1987 | Montgomery et al. |
| 4,662,374 | A | 5/1987 | Blake, III |
| 4,671,278 | A | 6/1987 | Chin |
| 4,671,282 | A | 6/1987 | Tretbar |
| 4,674,504 | A | 6/1987 | Klieman et al. |
| 4,681,107 | A | 7/1987 | Kees, Jr. |
| 4,696,396 | A | 9/1987 | Samuels |
| 4,702,247 | A | 10/1987 | Blake, III et al. |
| 4,706,668 | A | 11/1987 | Backer |
| 4,712,549 | A | 12/1987 | Peters et al. |
| 4,726,372 | A | 2/1988 | Perlin |
| 4,733,664 | A | 3/1988 | Kirsch et al. |
| 4,733,666 | A | 3/1988 | Mercer, Jr. |
| 4,759,364 | A | 7/1988 | Boebel |
| 4,765,335 | A | 8/1988 | Schmidt et al. |
| 4,777,949 | A | 10/1988 | Perlin |
| 4,777,950 | A | 10/1988 | Kees, Jr. |
| 4,796,625 | A | 1/1989 | Kees, Jr. |
| 4,799,481 | A | 1/1989 | Transue et al. |
| 4,815,466 | A | 3/1989 | Perlin |
| 4,817,604 | A | 4/1989 | Smith, III |
| 4,821,721 | A | 4/1989 | Chin et al. |
| 4,822,348 | A | 4/1989 | Casey |
| 4,827,930 | A | 5/1989 | Kees, Jr. |
| 4,834,096 | A | 5/1989 | Oh et al. |
| 4,850,355 | A | 7/1989 | Brooks et al. |
| 4,854,317 | A | 8/1989 | Braun |
| 4,856,517 | A | 8/1989 | Collins et al. |
| 4,929,239 | A | 5/1990 | Braun |
| 4,929,240 | A | 5/1990 | Kirsch et al. |
| 4,931,058 | A | 6/1990 | Cooper |
| 4,932,955 | A | 6/1990 | Merz et al. |
| 4,934,364 | A | 6/1990 | Green |
| 4,943,298 | A | 7/1990 | Fujita et al. |
| 4,957,500 | A | 9/1990 | Liang et al. |
| 4,966,603 | A | 10/1990 | Focelle et al. |
| 4,967,949 | A | 11/1990 | Sandhaus |
| 4,983,176 | A | 1/1991 | Cushman et al. |
| 4,988,355 | A | 1/1991 | Leveen et al. |
| 5,002,552 | A | 3/1991 | Casey |
| 5,026,379 | A | 6/1991 | Yoon |
| 5,030,224 | A | 7/1991 | Wright et al. |
| 5,030,226 | A | 7/1991 | Green et al. |
| 5,032,127 | A | 7/1991 | Frazee et al. |
| 5,035,692 | A | 7/1991 | Lyon et al. |
| 5,047,038 | A | 9/1991 | Peters et al. |
| 5,049,152 | A | 9/1991 | Simon et al. |
| 5,049,153 | A | 9/1991 | Nakao et al. |
| 5,053,045 | A | 10/1991 | Schmidt et al. |
| 5,059,202 | A | 10/1991 | Liang et al. |
| 5,062,846 | A | 11/1991 | Oh et al. |
| 5,078,731 | A | 1/1992 | Hayhurst |
| 5,084,057 | A | 1/1992 | Green et al. |
| 5,100,416 | A | 3/1992 | Oh et al. |
| 5,100,420 | A | 3/1992 | Green et al. |
| 5,104,394 | A | 4/1992 | Knoepfler |
| 5,104,395 | A | 4/1992 | Thornton et al. |
| 5,112,343 | A | 5/1992 | Thornton |
| 5,122,150 | A | 6/1992 | Puig |
| 5,127,915 | A | 7/1992 | Mattson |
| 5,129,885 | A | 7/1992 | Green et al. |
| 5,156,608 | A | 10/1992 | Troidl et al. |
| 5,160,339 | A | 11/1992 | Chen et al. |
| 5,163,945 | A | 11/1992 | Ortiz et al. |
| 5,171,247 | A | 12/1992 | Hughett et al. |
| 5,171,249 | A | 12/1992 | Stefanchik et al. |
| 5,171,250 | A | 12/1992 | Yoon |
| 5,171,251 | A | 12/1992 | Bregen et al. |
| 5,171,252 | A | 12/1992 | Friedland |
| 5,171,253 | A | 12/1992 | Klieman |
| 5,192,288 | A | 3/1993 | Thompson et al. |
| 5,197,970 | A | 3/1993 | Green et al. |
| 5,199,566 | A | 4/1993 | Ortiz et al. |
| 5,201,746 | A | 4/1993 | Shichman |
| 5,201,900 | A | 4/1993 | Nardella |
| 5,207,691 | A | 5/1993 | Nardella |
| 5,207,692 | A | 5/1993 | Kraus et al. |
| 5,217,473 | A | 6/1993 | Yoon |
| 5,219,353 | A | 6/1993 | Garvey, III et al. |
| 5,246,450 | A | 9/1993 | Thornton et al. |
| 5,269,792 | A | 12/1993 | Kovac et al. |
| 5,281,228 | A | 1/1994 | Wolfson |
| 5,282,807 | A | 2/1994 | Knoepfler |
| 5,282,808 | A | 2/1994 | Kovac et al. |
| 5,282,832 | A | 2/1994 | Toso et al. |
| 5,289,963 | A | 3/1994 | McGarry et al. |
| 5,290,299 | A | 3/1994 | Fain et al. |
| 5,300,081 | A | 4/1994 | Young et al. |
| 5,304,183 | A | 4/1994 | Gourlay et al. |
| 5,306,280 | A | 4/1994 | Bregen et al. |
| 5,306,283 | A | 4/1994 | Conners |
| 5,312,426 | A | 5/1994 | Segawa et al. |
| 5,330,442 | A | 7/1994 | Green et al. |
| 5,330,487 | A | 7/1994 | Thornton et al. |

(56) References Cited

U.S. PATENT DOCUMENTS

| | | |
|---|---|---|
| 5,340,360 A | 8/1994 | Stefanchik |
| 5,342,373 A | 8/1994 | Stefanchik et al. |
| 5,354,304 A | 10/1994 | Allen et al. |
| 5,354,306 A | 10/1994 | Garvey, III et al. |
| 5,356,064 A | 10/1994 | Green et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Fogelberg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,697,942 A | 12/1997 | Palti |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sheds et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,913,876 A | 6/1999 | Taylor et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi |
| 5,938,667 A | 8/1999 | Peyser et al. |
| 5,951,574 A | 9/1999 | Stefarichik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,044,971 A | 4/2000 | Esposito et al. |
| 6,053,908 A | 4/2000 | Crainich et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |

(56) References Cited

U.S. PATENT DOCUMENTS

| | | |
|---|---|---|
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,693 B2 | 1/2008 | Viola |
| 7,316,696 B2 | 1/2008 | Wilson, Jr. et al. |
| 7,320,692 B1 | 1/2008 | Bender et al. |
| 7,326,223 B2 | 2/2008 | Wilson, Jr. |
| 7,329,266 B2 | 2/2008 | Royse et al. |
| 7,331,968 B2 | 2/2008 | Arp et al. |
| 7,338,503 B2 | 3/2008 | Rosenberg et al. |
| 7,344,544 B2 | 3/2008 | Bender et al. |
| 7,357,805 B2 | 4/2008 | Masuda et al. |
| 7,357,806 B2 | 4/2008 | Rivera et al. |
| 7,407,074 B2 | 8/2008 | Ortiz et al. |
| 7,419,495 B2 | 9/2008 | Menn et al. |
| 7,431,724 B2 | 10/2008 | Manetakis et al. |
| 7,458,978 B1 | 12/2008 | Bender et al. |
| 7,473,258 B2 | 1/2009 | Clauson et al. |
| 7,485,124 B2 | 2/2009 | Kuhns et al. |
| 7,510,562 B2 | 3/2009 | Lindsay |
| 7,585,304 B2 | 9/2009 | Hughett |
| 7,637,917 B2 | 12/2009 | Whitfield et al. |
| 7,695,482 B2 | 4/2010 | Viola |
| 7,717,926 B2 | 5/2010 | Whitfield et al. |
| 7,819,886 B2 | 10/2010 | Whitfield et al. |
| 7,905,890 B2 | 3/2011 | Whitfield et al. |
| 7,988,027 B2 | 8/2011 | Olson et al. |
| 8,011,550 B2 | 9/2011 | Aranyi et al. |
| 8,011,555 B2 | 9/2011 | Tarinelli et al. |
| 8,016,178 B2 | 9/2011 | Olson et al. |
| 8,021,375 B2 | 9/2011 | Aldrich et al. |
| 8,021,378 B2 | 9/2011 | Sixto, Jr. et al. |
| 8,048,088 B2 | 11/2011 | Green et al. |
| 8,056,565 B2 | 11/2011 | Zergiebel |
| 8,070,760 B2 | 12/2011 | Fujita |
| 8,075,571 B2 | 12/2011 | Vitali et al. |
| 8,083,668 B2 | 12/2011 | Durgin et al. |
| 8,088,061 B2 | 1/2012 | Wells et al. |
| 8,091,755 B2 | 1/2012 | Kayan et al. |

(56) References Cited

U.S. PATENT DOCUMENTS

| | | |
|---|---|---|
| 8,128,643 B2 | 3/2012 | Aranyi et al. |
| 8,142,451 B2 | 3/2012 | Boulnois et al. |
| 8,157,149 B2 | 4/2012 | Olson et al. |
| 8,157,151 B2 | 4/2012 | Ingmanson et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,262,679 B2 | 9/2012 | Nguyen |
| 8,267,944 B2 | 9/2012 | Sorrentino et al. |
| 8,267,945 B2 | 9/2012 | Nguyen et al. |
| 8,267,946 B2 | 9/2012 | Whitfield et al. |
| 8,282,655 B2 | 10/2012 | Whitfield et al. |
| 8,328,822 B2 | 12/2012 | Huitema et al. |
| 8,336,556 B2 | 12/2012 | Zergiebel |
| 8,348,130 B2 | 1/2013 | Shah et al. |
| 8,357,171 B2 | 1/2013 | Whitfield et al. |
| 8,371,491 B2 | 2/2013 | Huitema et al. |
| 8,382,773 B2 | 2/2013 | Whitfield et al. |
| 8,403,138 B2 | 3/2013 | Weisshaupt et al. |
| 8,403,945 B2 | 3/2013 | Whitfield et al. |
| 8,403,946 B2 | 3/2013 | Whitfield et al. |
| 8,409,222 B2 | 4/2013 | Whitfield et al. |
| 8,409,223 B2 | 4/2013 | Sorrentino et al. |
| 8,419,752 B2 | 4/2013 | Sorrentino et al. |
| 8,430,892 B2 | 4/2013 | Bindra et al. |
| 8,444,660 B2 | 5/2013 | Adams et al. |
| 8,465,502 B2 | 6/2013 | Zergiebel |
| 8,475,473 B2 | 7/2013 | Vandenbroek et al. |
| 8,480,688 B2 | 7/2013 | Boulnois et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,512,357 B2 | 8/2013 | Viola |
| 8,523,882 B2 | 9/2013 | Huitema et al. |
| 8,529,585 B2 | 9/2013 | Jacobs et al. |
| 8,529,586 B2 | 9/2013 | Rosenberg et al. |
| 8,529,588 B2 | 9/2013 | Ahlberg et al. |
| 8,545,486 B2 | 10/2013 | Malkowski |
| 8,579,918 B2 | 11/2013 | Whitfield et al. |
| 8,585,717 B2 | 11/2013 | Sorrentino et al. |
| 8,603,109 B2 | 12/2013 | Aranyi et al. |
| 8,753,356 B2 | 6/2014 | Vitali et al. |
| 8,821,516 B2 | 9/2014 | Huitema |
| 8,828,023 B2 | 9/2014 | Neff et al. |
| 8,894,665 B2 | 11/2014 | Sorrentino et al. |
| 8,915,930 B2 | 12/2014 | Huitema et al. |
| 8,939,974 B2 | 1/2015 | Boudreaux et al. |
| 9,282,972 B1 | 3/2016 | Patel et al. |
| 9,445,810 B2 | 9/2016 | Cappola |
| 9,526,565 B2 | 12/2016 | Strobl |
| 9,717,504 B2 | 8/2017 | Huitema |
| 9,782,181 B2 | 10/2017 | Vitali et al. |
| 10,004,502 B2 | 6/2018 | Malkowski et al. |
| 10,136,939 B2 | 11/2018 | Minnelli et al. |
| 10,159,484 B2 | 12/2018 | Sorrentino et al. |
| 10,159,491 B2 | 12/2018 | Gokharu |
| 10,159,492 B2 | 12/2018 | Zammataro |
| 10,166,027 B2 | 1/2019 | Aranyi et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2001/0047178 A1 | 11/2001 | Peters |
| 2002/0068947 A1 | 6/2002 | Kuhns |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0123742 A1 | 9/2002 | Baxter et al. |
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto, Jr. et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | De Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake, III |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2004/0193213 A1 | 9/2004 | Aranyi |
| 2004/0232197 A1 | 11/2004 | Shelton et al. |
| 2005/0080440 A1 | 4/2005 | Durgin et al. |
| 2005/0085830 A1 | 4/2005 | Lehman et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0175703 A1 | 8/2005 | Hunter |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |

(56) References Cited

U.S. PATENT DOCUMENTS

| | | |
|---|---|---|
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0000867 A1 | 1/2006 | Shelton et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0111731 A1 | 5/2006 | Manzo |
| 2006/0124485 A1 | 6/2006 | Kennedy |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0241655 A1 | 10/2006 | Viola |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0021766 A1 | 1/2007 | Belagali et al. |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | De La Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093790 A1 | 4/2007 | Downey et al. |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118155 A1 | 5/2007 | Goldfarb et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santini et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0288039 A1 | 12/2007 | Aranyi |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2008/0015615 A1 | 1/2008 | Molitor et al. |
| 2008/0027465 A1 | 1/2008 | Vitali et al. |
| 2008/0027466 A1 | 1/2008 | Vitali et al. |
| 2008/0045978 A1 | 2/2008 | Kuhns et al. |
| 2008/0045981 A1 | 2/2008 | Margolin et al. |
| 2008/0051808 A1 | 2/2008 | Rivera et al. |
| 2008/0065118 A1 | 3/2008 | Damarati |
| 2008/0065119 A1 | 3/2008 | Viola |
| 2008/0114377 A1 | 5/2008 | Shibata et al. |
| 2008/0114378 A1 | 5/2008 | Matsushita |
| 2008/0125796 A1 | 5/2008 | Graham |
| 2008/0132915 A1 | 6/2008 | Buckman et al. |
| 2008/0140089 A1 | 6/2008 | Kogiso et al. |
| 2008/0140090 A1 | 6/2008 | Aranyi et al. |
| 2008/0147092 A1 | 6/2008 | Rogge et al. |
| 2008/0147093 A1 | 6/2008 | Roskopf et al. |
| 2008/0154287 A1 | 6/2008 | Rosenberg et al. |
| 2008/0167665 A1 | 7/2008 | Arp et al. |
| 2008/0188872 A1 | 8/2008 | Duff |
| 2008/0207995 A1 | 8/2008 | Kortenbach et al. |
| 2008/0208217 A1 | 8/2008 | Adams |
| 2008/0228199 A1 | 9/2008 | Cropper et al. |
| 2008/0228202 A1 | 9/2008 | Cropper et al. |
| 2008/0243143 A1 | 10/2008 | Kuhns et al. |
| 2008/0243145 A1 | 10/2008 | Whitfield et al. |
| 2008/0255589 A1 | 10/2008 | Blakeney et al. |
| 2008/0294178 A1 | 11/2008 | Kortenbach et al. |
| 2008/0306491 A1 | 12/2008 | Cohen et al. |
| 2008/0306492 A1 | 12/2008 | Shibata et al. |
| 2008/0306493 A1 | 12/2008 | Shibata et al. |
| 2008/0312665 A1 | 12/2008 | Shibata et al. |
| 2008/0312666 A1 | 12/2008 | Ellingwood et al. |
| 2008/0312670 A1 | 12/2008 | Lutze et al. |
| 2008/0319456 A1 | 12/2008 | Hart |
| 2009/0204115 A1 | 8/2009 | Dees, Jr. et al. |
| 2009/0261142 A1 | 10/2009 | Milliman et al. |
| 2009/0264904 A1 | 10/2009 | Aldrich et al. |
| 2009/0312775 A1 | 12/2009 | Gilkey et al. |
| 2010/0057105 A1 | 3/2010 | Sorrentino |
| 2010/0057107 A1 | 3/2010 | Sorrentino |
| 2010/0089970 A1 | 4/2010 | Smith et al. |
| 2010/0274262 A1 | 10/2010 | Schulz et al. |
| 2010/0318103 A1 | 12/2010 | Cheng et al. |
| 2010/0331862 A1 | 12/2010 | Monassevitch et al. |
| 2011/0087220 A1 | 4/2011 | Felder et al. |
| 2011/0087242 A1 | 4/2011 | Pribanic |
| 2011/0087268 A1 | 4/2011 | Livneh |
| 2011/0137323 A1 | 6/2011 | Malkowski et al. |
| 2011/0208212 A1 | 8/2011 | Zergiebel |
| 2011/0224701 A1 | 9/2011 | Menn |
| 2011/0245847 A1 | 10/2011 | Menn |
| 2012/0022526 A1 | 1/2012 | Aldridge et al. |
| 2012/0029534 A1 | 2/2012 | Whitfield |
| 2012/0109158 A1 | 5/2012 | Zammataro |
| 2012/0116420 A1 | 5/2012 | Sorrentino |
| 2012/0123446 A1 | 5/2012 | Aranyi |
| 2012/0197269 A1 | 8/2012 | Zammataro |
| 2012/0226291 A1 | 9/2012 | Malizia et al. |
| 2012/0253298 A1 | 10/2012 | Henderson et al. |
| 2012/0265220 A1 | 10/2012 | Menn |
| 2012/0277765 A1 | 11/2012 | Zammataro |
| 2012/0330326 A1 | 12/2012 | Creston |
| 2013/0041379 A1 | 2/2013 | Bodor et al. |
| 2013/0110135 A1 | 5/2013 | Whitfield |
| 2013/0131697 A1 | 5/2013 | Hartoumbekis |
| 2013/0165952 A1 | 6/2013 | Whitfield |

(56) References Cited

U.S. PATENT DOCUMENTS

| | | |
|---|---|---|
| 2013/0172910 A1 | 7/2013 | Malkowski |
| 2013/0172911 A1 | 7/2013 | Rockrohr |
| 2013/0172912 A1 | 7/2013 | Whitfield et al. |
| 2013/0175320 A1 | 7/2013 | Mandakolathur Vasudevan et al. |
| 2013/0190779 A1 | 7/2013 | Whitfield |
| 2013/0190780 A1 | 7/2013 | Whitfield et al. |
| 2013/0226200 A1 | 8/2013 | Kappel et al. |
| 2013/0253540 A1 | 9/2013 | Castro et al. |
| 2013/0274767 A1 | 10/2013 | Sorrentino et al. |
| 2013/0289583 A1 | 10/2013 | Zergiebel |
| 2013/0296891 A1 | 11/2013 | Hartoumbekis |
| 2013/0296892 A1 | 11/2013 | Sorrentino |
| 2013/0310849 A1 | 11/2013 | Malkowski |
| 2013/0325040 A1 | 12/2013 | Zammataro |
| 2013/0325057 A1 | 12/2013 | Larson et al. |
| 2014/0039526 A1 | 2/2014 | Malkowski |
| 2014/0052157 A1 | 2/2014 | Whitfield |
| 2014/0058412 A1 | 2/2014 | Aranyi |
| 2014/0074143 A1 | 3/2014 | Fitzgerald et al. |
| 2014/0188159 A1 | 7/2014 | Steege |
| 2014/0276970 A1 | 9/2014 | Messerly et al. |
| 2014/0371728 A1 | 12/2014 | Vaughn |
| 2015/0201953 A1 | 7/2015 | Strobl et al. |
| 2015/0265282 A1 | 9/2015 | Miles et al. |
| 2015/0313452 A1 | 11/2015 | Nasser et al. |
| 2015/0314451 A1 | 11/2015 | Nixon |
| 2016/0004956 A1 | 1/2016 | Reynolds et al. |
| 2016/0030044 A1 | 2/2016 | Zammataro |
| 2017/0049449 A1 | 2/2017 | Aranyi et al. |
| 2017/0065277 A1 | 3/2017 | Malkowski |
| 2017/0065281 A1 | 3/2017 | Zammataro |
| 2017/0086846 A1 | 3/2017 | Sorrentino et al. |
| 2017/0086850 A1 | 3/2017 | Zergiebel |
| 2017/0128071 A1 | 5/2017 | Holsten et al. |
| 2017/0202567 A1 | 7/2017 | Griffiths et al. |
| 2017/0245921 A1 | 8/2017 | Joseph et al. |
| 2017/0252042 A1 | 9/2017 | Kethman et al. |
| 2017/0290587 A1 | 10/2017 | Schober et al. |
| 2018/0021041 A1 | 1/2018 | Zhang et al. |
| 2018/0168660 A1 | 6/2018 | Gokharu |
| 2018/0214156 A1 | 8/2018 | Baril et al. |
| 2018/0221028 A1 | 8/2018 | Williams |
| 2018/0228492 A1 | 8/2018 | Aranyi et al. |
| 2018/0228567 A1 | 8/2018 | Baril et al. |
| 2018/0235632 A1 | 8/2018 | Mujawar et al. |
| 2018/0235633 A1 | 8/2018 | Baril et al. |
| 2018/0235637 A1 | 8/2018 | Xu et al. |
| 2018/0242977 A1 | 8/2018 | Tan et al. |
| 2018/0263624 A1 | 9/2018 | Malkowski et al. |
| 2018/0271526 A1 | 9/2018 | Zammataro |
| 2018/0317927 A1 | 11/2018 | Cal et al. |
| 2018/0317928 A1 | 11/2018 | P V R |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czemik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| CN | 103251441 A | 8/2013 |
| CN | 104605911 B | 2/2017 |
| DE | 202007003398 U1 | 6/2007 |
| DE | 20 2009 006113 U1 | 7/2009 |
| EP | 0085931 A2 | 8/1983 |
| EP | 0086721 A2 | 8/1983 |
| EP | 0324166 A2 | 7/1989 |
| EP | 0392750 A1 | 10/1990 |
| EP | 0569223 A1 | 11/1993 |
| EP | 0594003 A1 | 4/1994 |
| EP | 0598529 A2 | 5/1994 |
| EP | 0685204 A1 | 12/1995 |
| EP | 0732078 A2 | 9/1996 |
| EP | 0755655 A2 | 1/1997 |
| EP | 0769274 A1 | 4/1997 |
| EP | 0769275 A1 | 4/1997 |
| EP | 0834286 A1 | 4/1998 |
| EP | 1317906 A1 | 6/2003 |
| EP | 1609427 A1 | 12/2005 |
| EP | 1712187 A2 | 10/2006 |
| EP | 1712191 A2 | 10/2006 |
| EP | 1757236 A2 | 2/2007 |
| EP | 1813199 A1 | 8/2007 |
| EP | 1908423 A2 | 4/2008 |
| EP | 1913881 A1 | 4/2008 |
| EP | 2229895 A1 | 9/2010 |
| EP | 2332471 A1 | 6/2011 |
| EP | 3132756 A1 | 2/2017 |
| JP | 2003033361 A | 2/2003 |
| JP | 2011186812 A | 9/2011 |
| JP | 2013166982 A | 8/2013 |
| WO | 9003763 A1 | 4/1990 |
| WO | 0042922 A1 | 7/2000 |
| WO | 0166001 A2 | 9/2001 |
| WO | 0167965 A1 | 9/2001 |
| WO | 03086207 A1 | 10/2003 |
| WO | 03092473 A2 | 11/2003 |
| WO | 2005091457 A1 | 9/2005 |
| WO | 2006042076 A2 | 4/2006 |
| WO | 2006042084 A2 | 4/2006 |
| WO | 2006042110 A2 | 4/2006 |
| WO | 2006042141 A2 | 4/2006 |
| WO | 2006135479 A2 | 12/2006 |
| WO | 2008118928 A2 | 10/2008 |
| WO | 2008127968 A2 | 10/2008 |
| WO | 2016192096 A1 | 12/2016 |
| WO | 2016192718 A2 | 12/2016 |
| WO | 2016197350 A1 | 12/2016 |
| WO | 2016206015 A1 | 12/2016 |
| WO | 2017084000 A1 | 5/2017 |
| WO | 2017146138 A1 | 8/2017 |

OTHER PUBLICATIONS

International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.

(56) References Cited

OTHER PUBLICATIONS

International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appin. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.
Extended European Search Report corresponding to Patent Application EP 18154617.7 dated Jun. 25, 2018.
Extended European Search Report corresponding to Patent Application EP 18155158.1 dated Jun. 28, 2018.
Extended European Search Report corresponding to Patent Application EP 15877428.1 dated Jul. 2, 2018.
Extended European Search Report corresponding to Patent Application EP 18157789.1 dated Jul. 5, 2018.
Canadian Office Action corresponding to Patent Application CA 2,972,444 dated Aug. 9, 2018.
Extended European Search Report corresponding to Patent Application EP 18156458.4 dated Sep. 3, 2018.
Extended European Search Report corresponding to Patent Application EP 18171682.0 dated Sep. 18, 2018.
Extended European Search Report corresponding to Patent Application EP 15878354.8 dated Sep. 19, 2018.
Extended European Search Report corresponding to Patent Application EP 18183394.8 dated Sep. 28, 2018.
Extended European Search Report corresponding to Patent Application EP 18163041.9 dated Sep. 28, 2018.
Extended European Search Report corresponding to Patent Application EP 18170524.5 dated Oct. 1, 2018.
Japanese Office Action corresponding to Patent Application JP 2017-536546 dated Oct. 15, 2018.
Extended European Search Report corresponding to Patent Application EP 18187640.0 dated Nov. 30, 2018.
Extended European Search Report corresponding to Patent Application EP 18187690.5 dated Nov. 30, 2018.
Chinese First Office Action corresponding to Patent Application CN 201510696298.9 dated Dec. 3, 2018.
Extended European Search Report corresponding to Patent Application EP 18158143.0 dated Dec. 5, 2018.

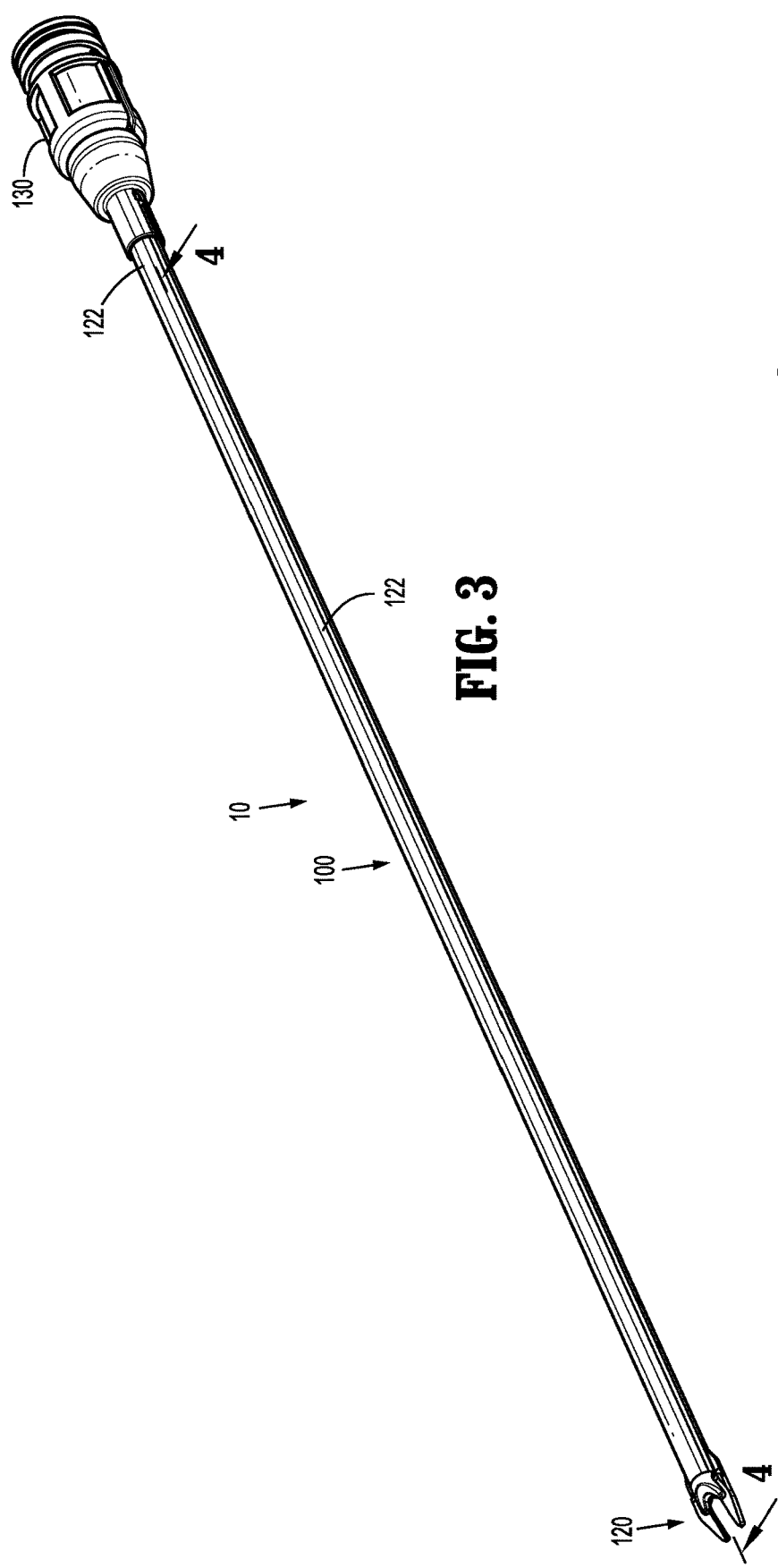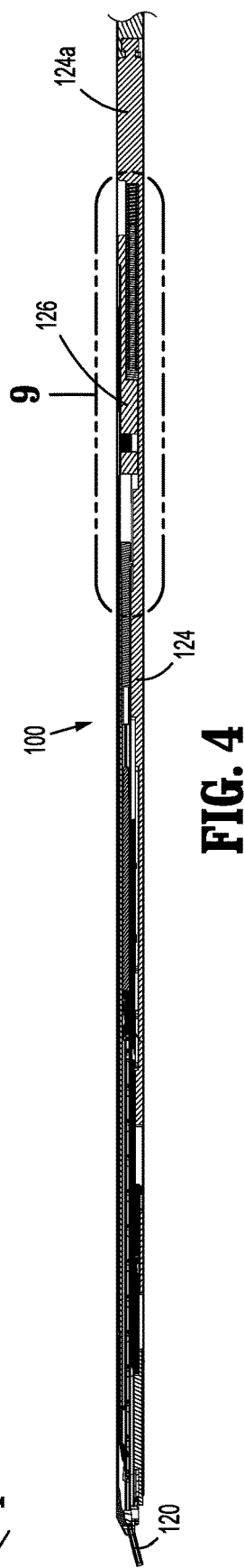

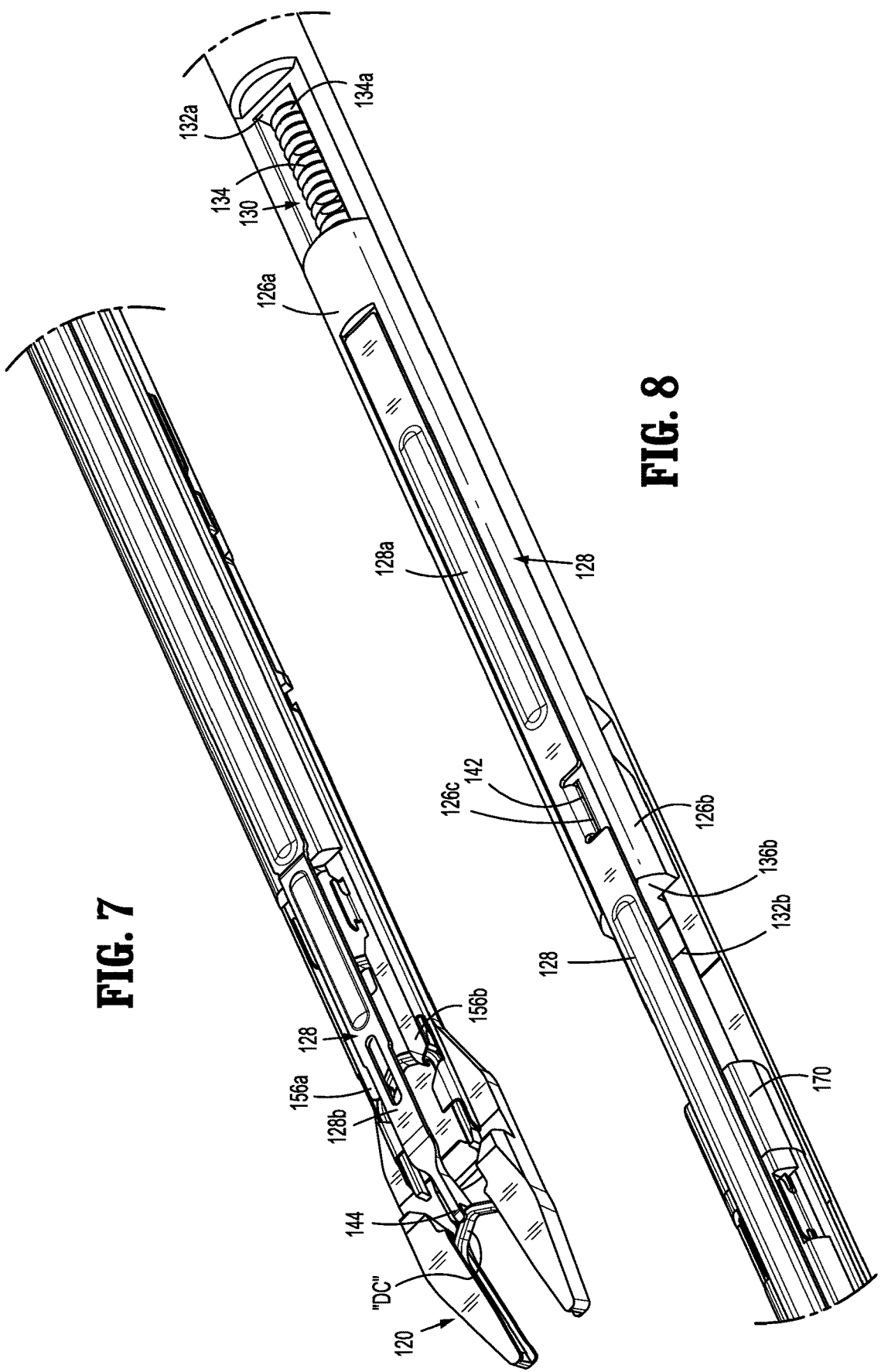

ENDOSCOPIC SURGICAL CLIP APPLIER

CROSS-REFERENCE TO RELATED APPLICATIONS

This application claims the benefit of and priority to U.S. Provisional Patent Application No. 62/542,325 filed Aug. 8, 2017, the entire disclosure of which is incorporated by reference herein.

BACKGROUND

Technical Field

The present application relates generally to surgical clip appliers. More particularly, the present disclosure relates to endoscopic surgical clip appliers having a clip pusher bar that maintains a surgical clip between jaws of the surgical clip applier during clip formation.

Description of Related Art

Endoscopic surgical staplers and surgical clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often use a particular endoscopic surgical clip applier to apply a surgical clip to a blood vessel or another duct to prevent the flow of body fluids therethrough during the procedure.

Endoscopic surgical clip appliers having various sizes (e.g., diameters) that are configured to apply a variety of diverse surgical clips are known in the art, and which are capable of applying a single or multiple surgical clips during an entry to the body cavity. Such surgical clips are typically fabricated from a biocompatible material and are usually compressed over a vessel. Once applied to the vessel, the compressed surgical clip terminates the flow of fluid therethrough.

Endoscopic surgical clip appliers that are able to apply multiple clips in endoscopic or laparoscopic procedures during a single entry into the body cavity are described in commonly-assigned U.S. Pat. Nos. 5,084,057 and 5,100,420, which are both incorporated by reference herein in their entirety. Another multiple endoscopic surgical clip applier is disclosed in commonly-assigned U.S. Pat. No. 5,607,436, the contents of which are also hereby incorporated by reference herein in its entirety. These devices are typically, though not necessarily, used during a single surgical procedure. U.S. Pat. No. 5,695,502, the disclosure of which is hereby incorporated by reference herein, discloses a resterilizable endoscopic surgical clip applier. The endoscopic surgical clip applier advances and forms multiple clips during a single insertion into the body cavity. This resterilizable endoscopic surgical clip applier is configured to receive and cooperate with an interchangeable clip magazine so as to advance and form multiple clips during a single entry into a body cavity.

Sometimes prior to or during formation of the clip, the clip may be prematurely dislocated from between the jaws of the clip applier by, for example, the vessel being closed. Accordingly, a need exists for a clip applier having an improved mechanism that prevents clip dislocation during use.

SUMMARY

Accordingly, the present application provides an apparatus for application of surgical clips to body tissue. The apparatus includes a handle assembly and a shaft assembly selectively connectable to the handle assembly and actuatable upon actuation of the handle assembly. The shaft assembly includes a pair of jaws movable between a spaced-apart position and an approximated position, an elongated spindle, a trip block, a biasing member, and a pusher bar. The spindle has a proximal portion configured to be coupled to an actuator, and a distal portion operably coupled to the pair of jaws to selectively approximate the pair of jaws during distal advancement of the spindle. The trip block is reciprocally supported on the proximal portion of the spindle and axially movable both with and relative to the spindle. The biasing member extends between the proximal portion of the spindle and the trip block. The pusher bar has a proximal portion fixedly coupled to the trip block, and a distal portion configured to load a distal-most surgical clip into the pair of jaws during distal movement of the trip block, via distal movement of the spindle, and remain in a distally advanced position during approximation of the pair of jaws.

In embodiments, both the trip block and the pusher bar may be configured to move with the spindle in response to a first distal movement of the spindle to engage the distal portion of the pusher bar with the distal-most surgical clip. Movement of both the trip block and the pusher bar with the spindle may be resisted during a second distal movement of the spindle.

It is contemplated that the shaft assembly may further include a clip channel slidably retaining a stack of surgical clips. The clip channel may include the distal-most surgical clip therein and have a distal stop that couples to the distal portion of the pusher bar via the distal-most surgical clip after the first distal movement of the spindle. The distal stop may resist both the trip block and the pusher bar from advancing distally during the second distal movement of the spindle.

It is envisioned that the second distal movement of the spindle may compress the biasing member between the spindle and the trip block to increase a spring force of the biasing member. The spring force of the biasing member may exceed a holding force exerted on the distal-most surgical clip by the distal stop of the clip channel upon the spindle completing the second distal movement, such that the trip block and the pusher bar are moved distally relative to the spindle via the biasing member to position the distal-most surgical clip between the pair of jaws.

In embodiments, the pair of jaws may be configured to form the distal-most surgical clip in response to a third distal movement of the spindle while the distal portion of the pusher bar is maintained in engagement with the distal-most surgical clip by the biasing member.

It is contemplated that the distal stop of the clip channel may include a resilient tang that captures the distal-most clip to resist distal movement of the distal-most surgical clip relative thereto.

It is envisioned that the biasing member may be in a preloaded condition prior to the first distal movement of the spindle to distally bias the trip block and the pusher bar relative to the spindle.

In embodiments, the proximal portion of the spindle may define an elongate channel, and the trip block may define an elongate channel in communication with the elongate channel of the spindle. The elongate channel of each of the spindle and the trip block may have the biasing member extending therethrough.

It is contemplated that the proximal portion of the spindle may have a distally-oriented wall having a proximal portion of the biasing member coupled thereto, and the trip block may have a proximally-oriented wall having a distal portion of the biasing member coupled thereto.

It is envisioned that the pusher bar may include a fin extending laterally from the proximal portion thereof, and the trip block may define a notch having the fin of the pusher bar received therein.

In embodiments, the shaft assembly may include a stop axially fixed relative to the pair of jaws, and the trip block may have a distal portion configured to contact the stop upon the trip block moving to a distal position, such that the stop resists further distal movement of the pusher bar.

It is contemplated that the distal portion of the pusher bar may position the distal-most surgical clip between the pair of jaws when the trip block is in the distal position.

It is envisioned that the shaft assembly may include an outer member having the stop axially fixed therein.

In embodiments, the spindle may define a longitudinally-extending channel through which a distal portion of the trip block axially moves. The channel of the spindle may have a distal limit that contacts the distal portion of the trip block during proximal retraction of the spindle.

It is contemplated that the pusher bar may include a pusher formed at a distal end thereof. The pusher may have a narrow profile for allowing the pair of jaws to move to the approximated position while the pusher is disposed therebetween.

In another aspect of the present disclosure, a shaft assembly of an apparatus for applying surgical clips to body tissue is provided. The shaft assembly includes an elongated spindle, a trip block, a biasing member, and a pusher bar. The elongated spindle has a proximal portion configured to be coupled to an actuator, and a distal portion configured to be operably coupled to a pair of jaws to selectively approximate the pair of jaws during distal advancement of the spindle. The trip block is reciprocally supported on the proximal portion of the spindle and axially movable both with and relative to the spindle. The biasing member extends between the proximal portion of the spindle and the trip block. The pusher bar has a proximal portion fixedly coupled to the trip block, and a distal portion configured to load a distal-most surgical clip into the pair of jaws during distal movement of the trip block, via distal movement of the spindle, and remain in a distally advanced position during approximation of the pair of jaws.

BRIEF DESCRIPTION OF THE DRAWINGS

A particular embodiment of a surgical clip applier is disclosed herein with reference to the drawings wherein:

FIG. 3 is a perspective view of the shaft assembly of the endoscopic surgical clip applier of FIG. 1;

FIG. 4 is a cross-sectional view, taken alone line 4-4 of FIG. 3, illustrating inner components of the shaft assembly;

FIG. 7 is an enlarged view of the area of detail labeled "7" in FIG. 6, illustrating a distal portion of the shaft assembly;

FIG. 8 is an enlarged view of the area of detail labeled "8" in FIG. 6, illustrating a proximal portion of the shaft assembly;

DETAILED DESCRIPTION

Figure 1:
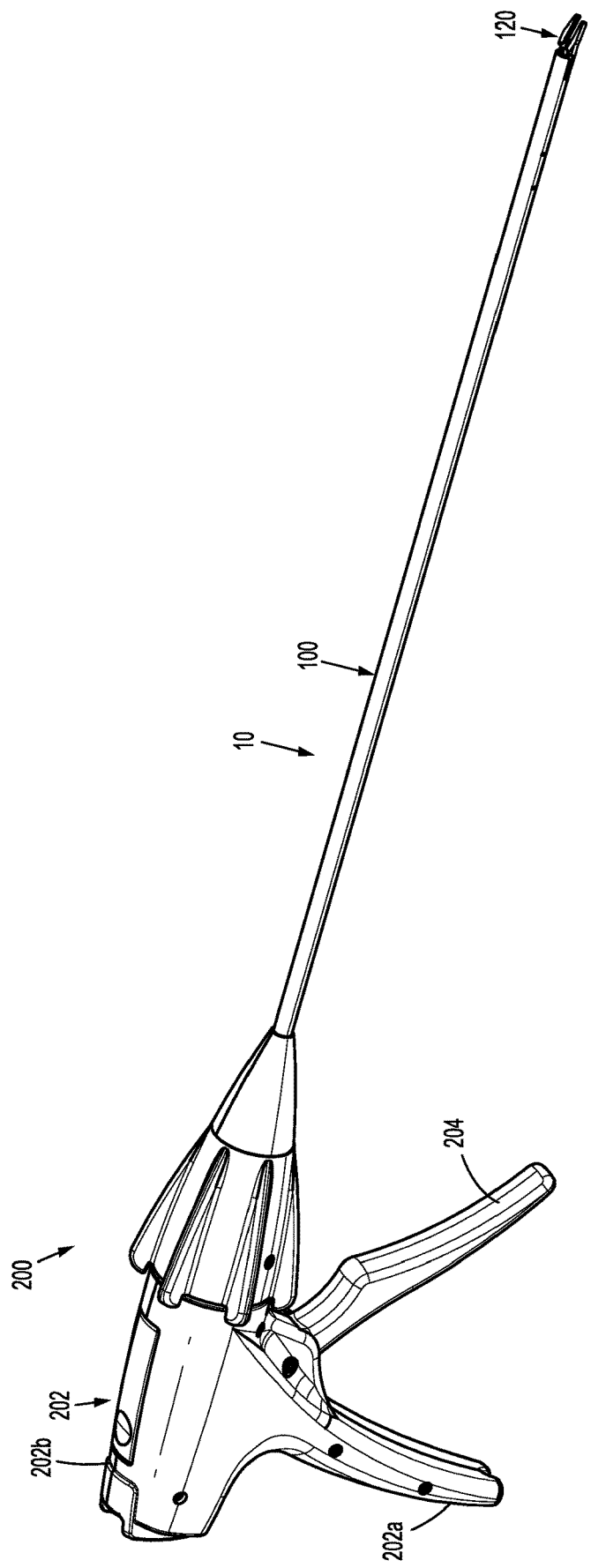
FIG. 1 is a perspective view of a reposable endoscopic surgical clip applier including a reusable handle assembly and a shaft assembly connected thereto.

Embodiments of endoscopic surgical clip appliers and shaft assemblies thereof, in accordance with the present disclosure, will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Figure 2:
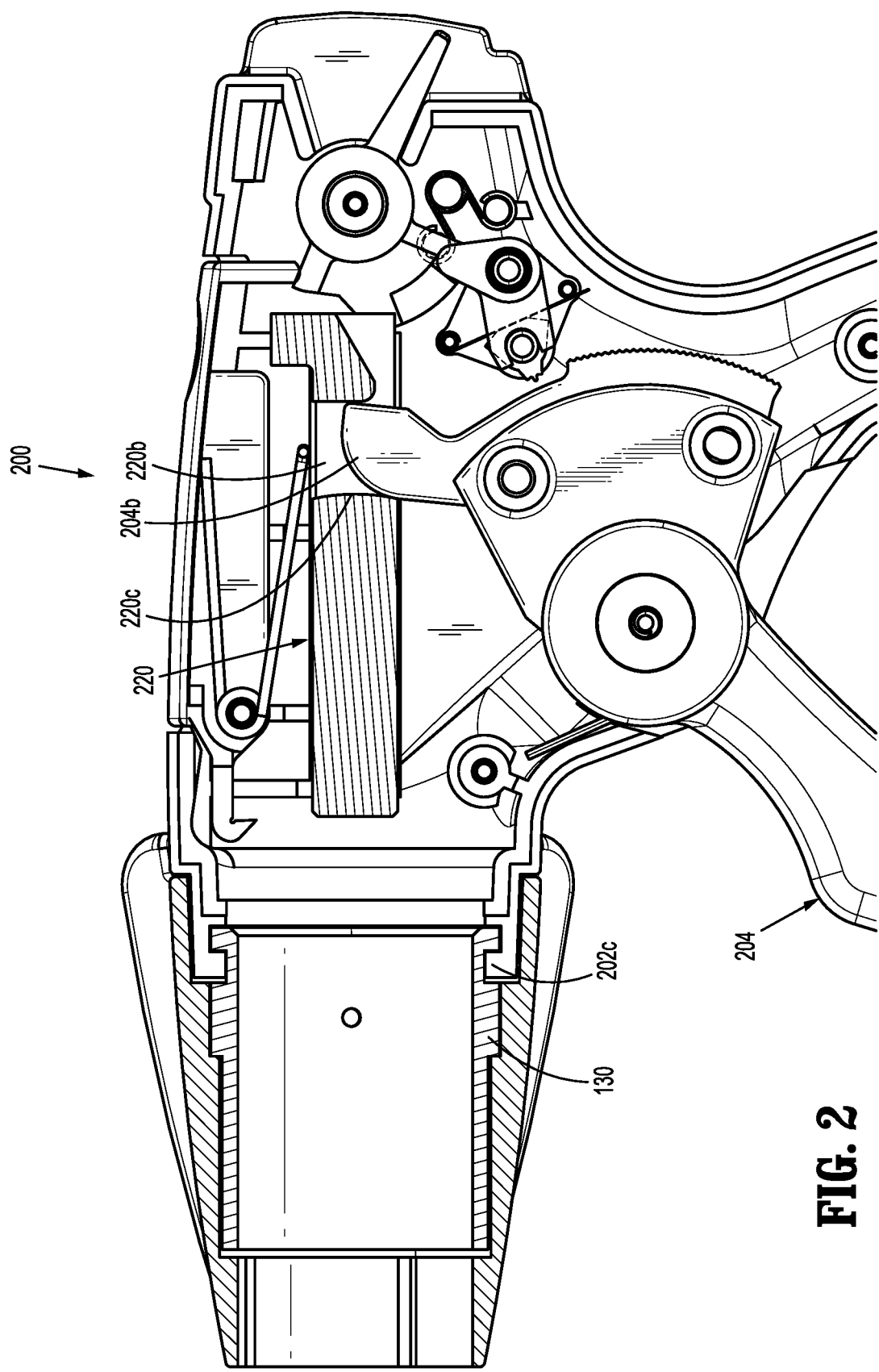
FIG. 2 is a perspective view of the handle assembly of FIG. 1 with at least a housing half-section removed therefrom.

With reference to FIGS. 1 and 2, an apparatus for application of surgical clips to body tissue is illustrated and designated 10. The apparatus or surgical clip applier 10 generally includes a reusable handle assembly 200 and a disposable shaft assembly 100 operably coupled to the handle assembly 200. The handle assembly 200 includes a housing 202 having a first or right side half-section 202a and a second or left side half-section 202b. Housing 202 of handle assembly 200 further includes or defines a nose 202c dimensioned for receipt of a hub 130 of shaft assembly 100. Housing 202 of handle assembly 200 may be formed of a suitable plastic or thermoplastic material. It is further contemplated that housing 202 of handle assembly 200 may be fabricated from stainless steel of the like.

Handle assembly 200 includes a trigger 204 pivotably supported between right side half-section 202a and left side half-section 202b of housing 202. Trigger 204 is biased by a biasing member (not explicitly shown) to bias or urge trigger 204 to the un-actuated condition. Trigger 204 includes a drive arm 204b extending therefrom. Drive arm 204b may be integrally formed therewith or may be separately and fixedly secured to trigger 204. Drive arm 204b may define a curved, radiused or filleted upper distal surface.

Handle assembly 200 further includes a drive plunger 220 operatively connected to trigger 204. Drive plunger 220 defines a proximally extending trigger slot 220b formed in a proximal portion thereof for operatively receiving drive arm 204b of trigger 204. Trigger slot 220b defines a distal surface or wall 220c against which a distal surface of drive arm 204b of trigger 204 contacts in order to distally advance drive plunger 220 during an actuation of trigger 204. Drive plunger 220 has a distal end operably coupled to a proximal end of a spindle 124 (FIG. 5) of shaft assembly 100 to effect axial movement of the spindle 124 upon actuation of the trigger 204 of handle assembly 200.

For a more detailed description of the components and operation of the handle assembly 200 of clip applier 10, reference may be made to, for example, U.S. Patent Application Publication No. 2017/0128071, the entire contents of which being incorporated by reference herein.

Figure 5:
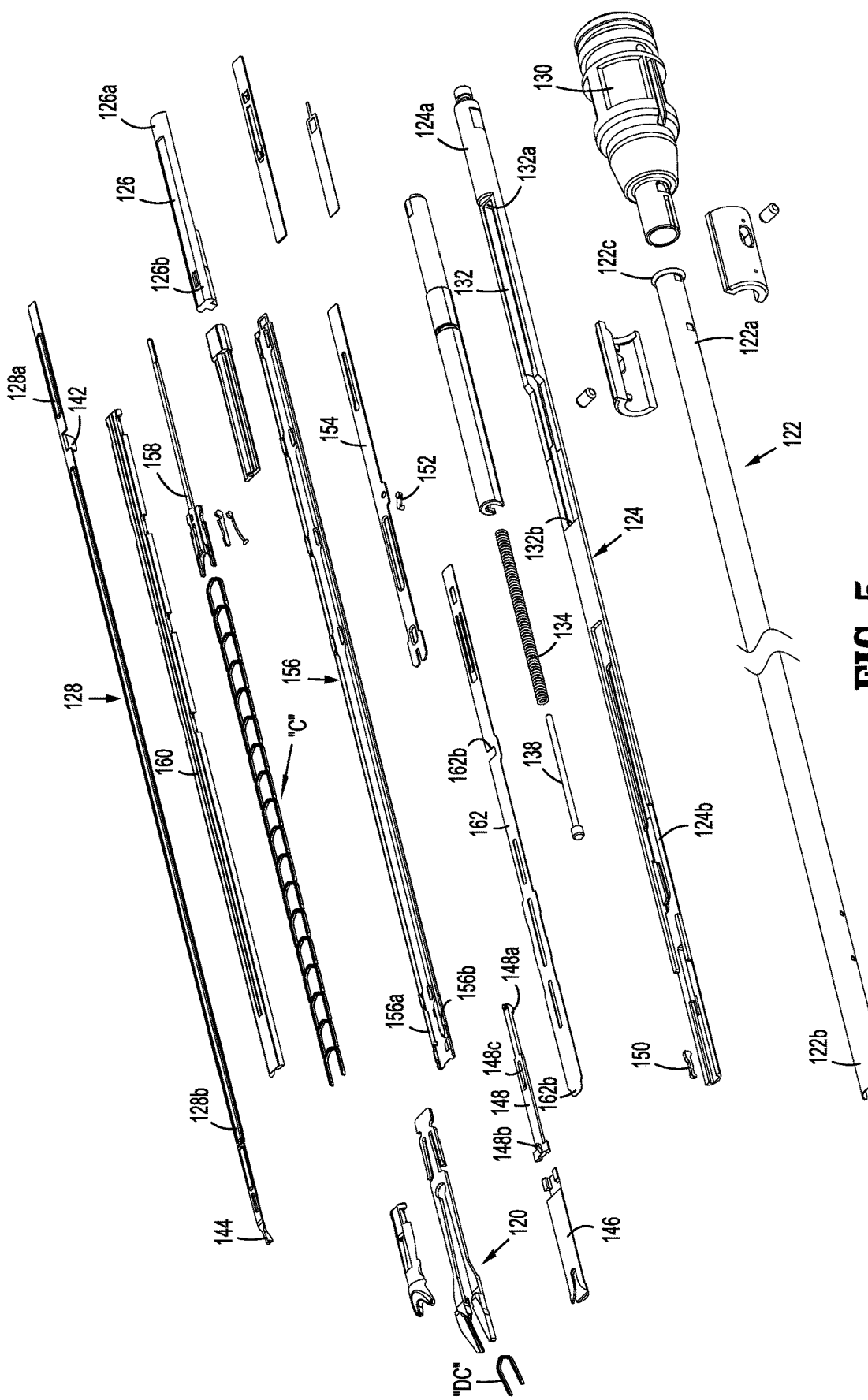
FIG. 5 is a perspective view, with parts separated, of the shaft assembly of FIG. 3.
Figure 6:
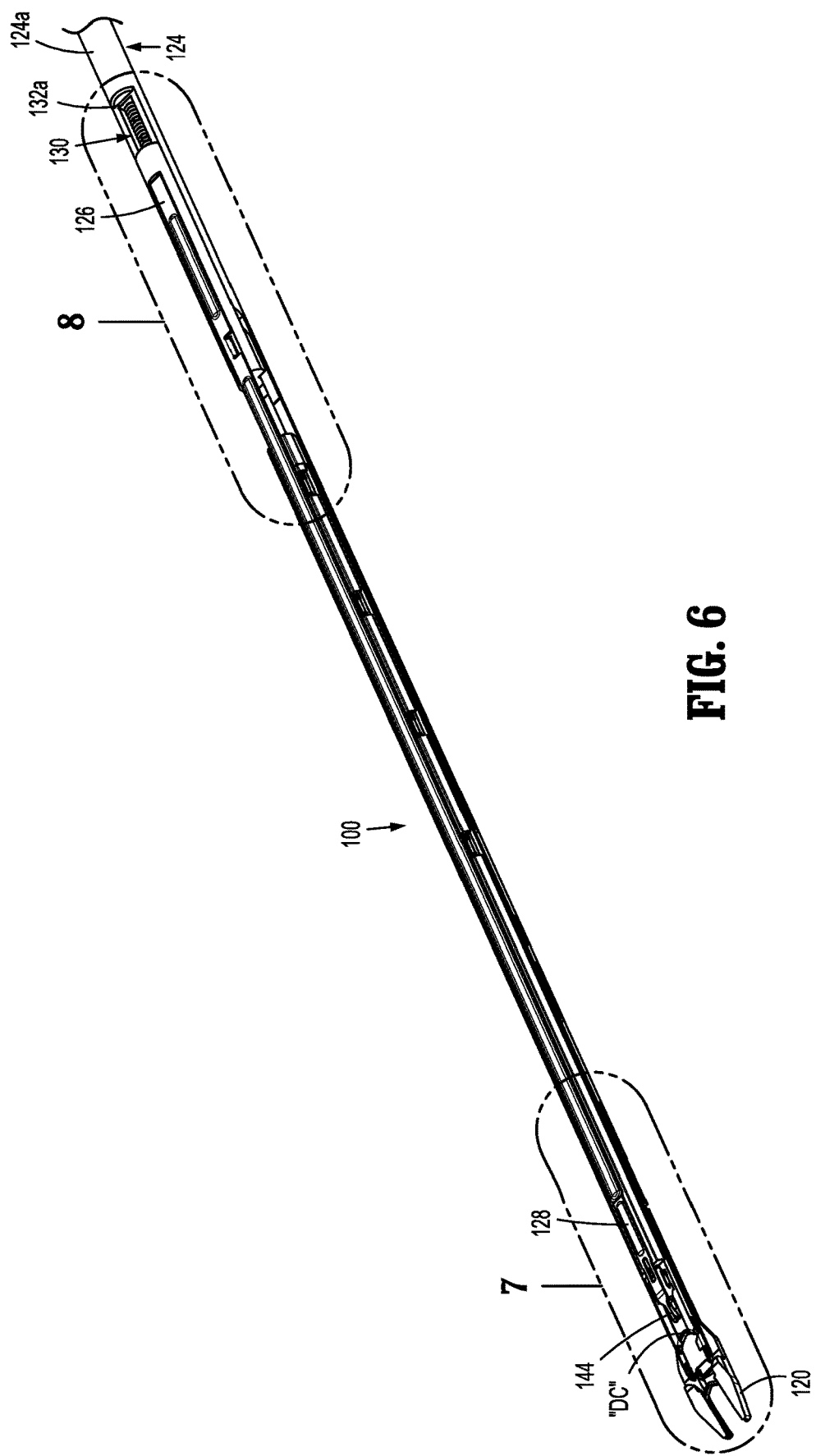
FIG. 6 is a perspective view, with parts assembled, of the inner components of the shaft assembly of FIG. 3.
Figure 9:
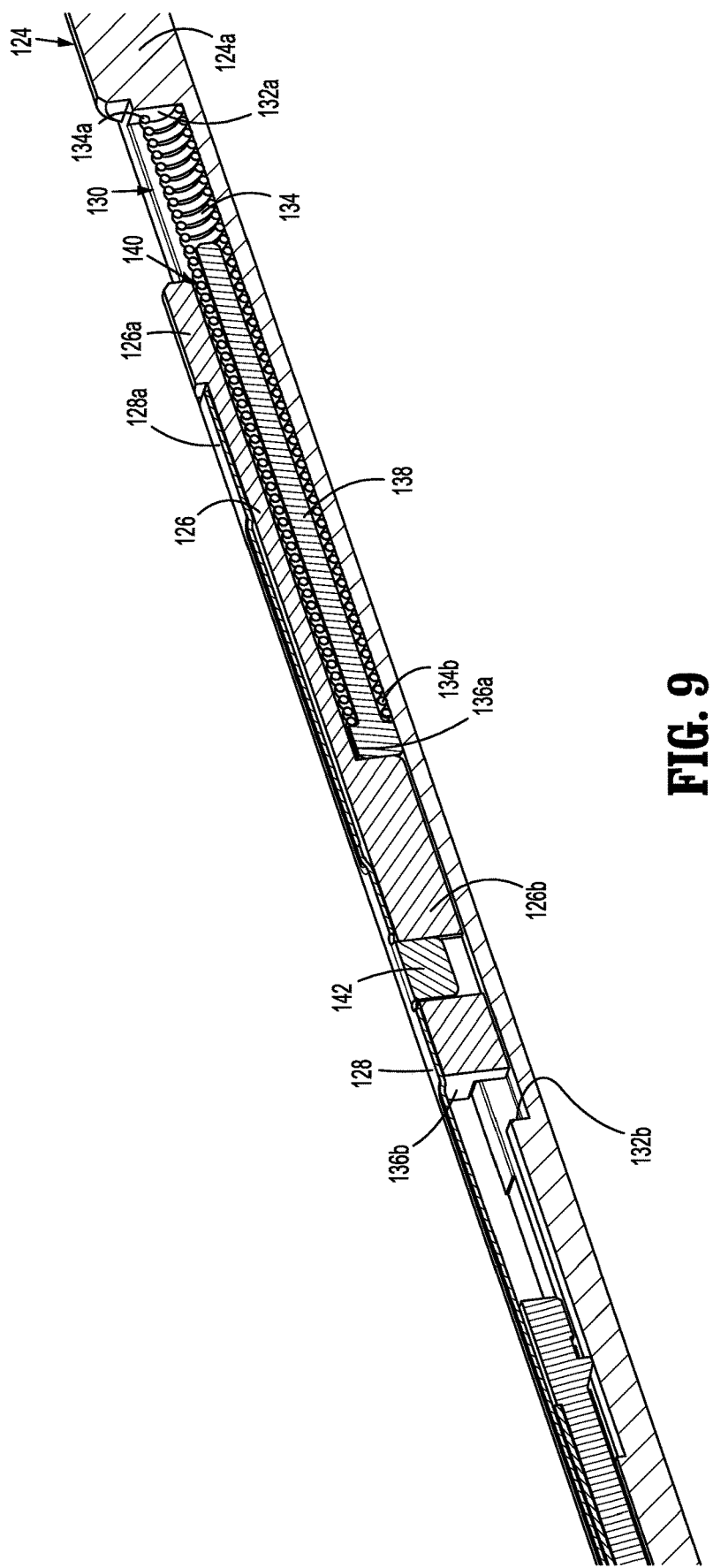
FIG. 9 is an enlarged view of the area of detail labeled "9" in FIG. 4, illustrating a trip block, a pusher, and a biasing member of the shaft assembly in an advanced position.
Figure 10:
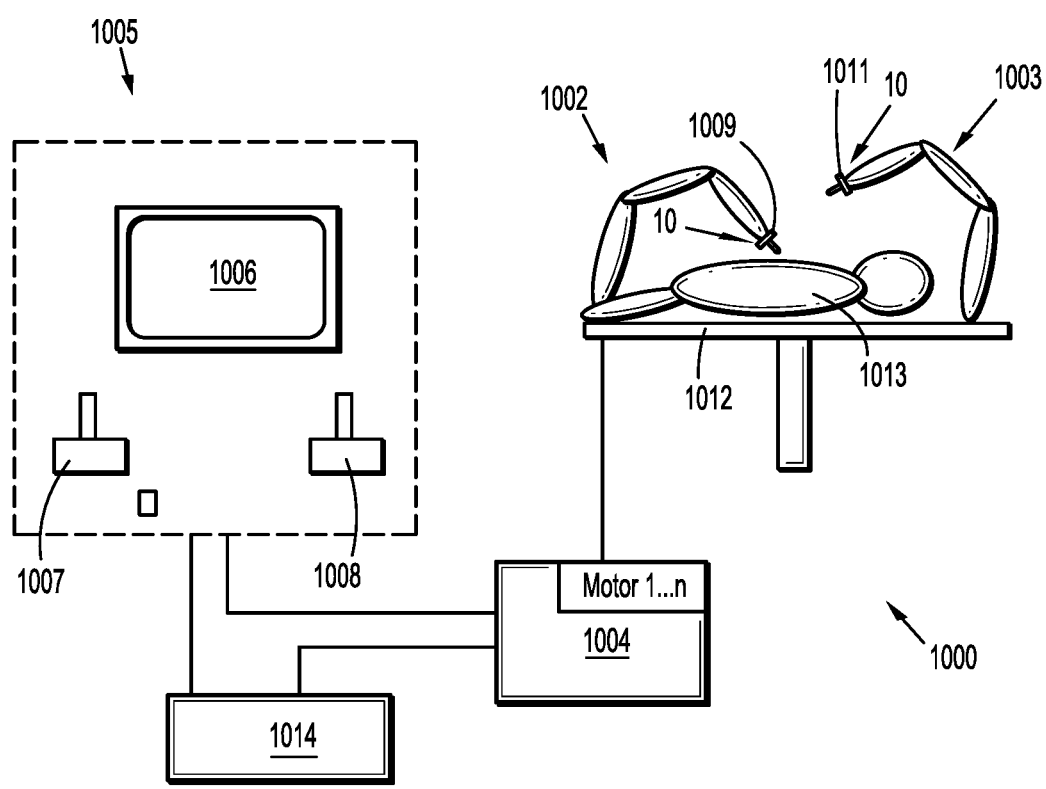
FIG. 10 is a schematic illustration of a robotic surgical system configured for use in accordance with the present disclosure.

With reference to FIGS. 3-5, the shaft assembly 100 of the clip applier 10 is operably coupled to the handle assembly 200 for actuation by the handle assembly 200. The shaft assembly 100 stores a stack of surgical clips "C" therein and has a pair of jaws 120 configured to form, in seriatim, the surgical clips "C" received from a pusher bar 128 of the shaft assembly 120 upon actuation of the handle assembly 200. The shaft assembly 100 includes an elongated outer member or outer tube 122, an elongated spindle or inner shaft 124 axially movable within the outer tube 122 for actuating the clip applier 10, and a trip block 126 movably coupled to the spindle 124 for axially translating a pusher bar 128 to load and hold the surgical clips "C" in the jaws 120 during clip formation, as will be described. The outer tube 122 of the shaft assembly 100 has a proximal portion 122a supported and secured to a hub 130, and a distal portion 122b supporting the jaws 120. The hub 130 may be configured to be coupled to the handle assembly 200 (FIGS. 1 and 2) or an actuator of a robotic system 1000 (FIG. 10). The outer tube 122 defines a lumen 122c extending longitudinally therethrough dimensioned for slidable receipt of the spindle 124.

With reference to FIGS. 5-9, the spindle or inner shaft 124 is slidably supported within the lumen 122c of the outer tube 122 and has a generally elongated configuration. The spindle 124 includes a proximal portion 124a, and a distal portion 124b configured to selectively actuate the pair of jaws 120 during distal advancement of the spindle 124. The proximal portion 124a of the spindle 124 may define a hook, an enlarged head or other translational force coupling feature configured to be coupled to an actuator (e.g., the drive plunger 220 of the handle assembly 200 or an actuator of the robotic surgical system 1000). The proximal portion 124a of the spindle 124 defines an elongate channel 132 extending longitudinally along the spindle 124. The channel 132 of the spindle 124 has proximal and distal limits defined respectively by proximal and distal walls 132a, 132b.

The proximal portion 124a of the spindle 124 supports a biasing member 134 (e.g., a coil spring) disposed within the channel 132 of the spindle 124. The biasing member 134 has a proximal portion 134a fixed to the proximal wall 132a of the proximal portion 124a of the spindle 124, and a distal portion 134b coupled to a wall 136a defined by the trip block 126. The biasing member 134 is held within the channel 132 of the spindle 124 between the proximal wall 132a of the proximal portion 124a of the spindle 124 and the wall 136 of the trip block 126 in a preloaded condition so as to exert a distally-oriented resilient bias on the trip block 126 relative to the spindle 124. The biasing member 134 may have a rod member 138 extending through a central passageway thereof to maintain the biasing member 134 in a linear configuration (e.g., to prevent buckling).

The trip block 126 of the shaft assembly 100 has an elongated configuration and is reciprocally supported on the proximal portion 124a of the spindle 124 and axially movable both with and relative to the spindle 124. In particular, the trip block 126 includes a proximal portion 126a supported on an upper surface of the proximal portion 124a of the spindle 124, and a distal portion 124b movably received in the channel 132 of the spindle 124. The trip block 126 defines an elongate channel 140 (FIG. 9) in communication with the channel 132 of the spindle 124, whereby the channels 132, 140 of the spindle 124 and the trip block 126, respectively, together form a unitary channel in which the biasing member 134 is disposed.

The distal portion 126b of the trip block 126 has a proximally-oriented wall 136a having the distal portion 134b of the biasing member 134 coupled thereto. As briefly mentioned above, the biasing member 134 is fixed at its proximal portion 134a to the proximal wall 132a of the spindle 124, such that the biasing member 134 exerts a distally-oriented resilient bias on the trip block 126 relative to the spindle 124. In this way, a first distal advancement of the spindle 124 results in the concomitant distal advancement of the trip block 126. The distal portion 126b of the trip block also has a distally-oriented wall 136b configured to contact the distal wall 132b of the spindle 124 during retraction of the spindle 124, as will be described in detail below. A block or stop 170 is disposed distally of the trip block 126 and axially fixed within and relative to the outer tube 122 for providing a distal limit to the axial movement of the trip block 126. The stop 170 resists the trip block 126 and the pusher bar 128 from advancing distally beyond the stop 170 upon the distally-oriented wall 136b of the trip block 126 contacting the stop 170.

The distal portion of the trip block 126 defines a notch 126c therein for receiving a proximal portion 128a of the pusher bar 128. The pusher bar 128 has a proximal portion 128a, and a distal portion 128b for loading a distal-most surgical clip "DC" of the stack of surgical clips "C" between the jaws 120. The proximal portion 128a of the pusher bar 128 includes a fin 142 extending laterally therefrom, which is received in the notch 126c of the distal portion 126b of the trip block 126 for fixing the pusher bar 128 to the trip block 126 so that the pusher bar 128 moves axially with axial movement of the trip block 126. In embodiments, the proximal portion 128a of the pusher bar 128 may be fixed to the distal portion 126b of the trip block 126 via any suitable fastening engagement, such as, for example, various fasteners, adhesives, snap-fit engagements, or the like. Since the proximal portion 128a of the pusher bar 128 is fixed to the distal portion 126b of the trip block 126, axial movement of the trip block 126 results in a corresponding axial movement of the pusher bar 128.

The distal portion 128b of the pusher bar 128 defines a pusher 144 configured to position the distal-most surgical clip "DC" between the pair of jaws 120 as the trip block 126 is advanced toward a distal position, as shown in FIG. 7. The pusher 144 has a narrow profile for allowing the pair of jaws 120 to move to an approximated position while the pusher 144 is disposed therebetween. For example, the pusher 144 may have a width that is less than a horizontal distance the pair of jaws 120 are spaced from one another after completing a clip formation.

With continued reference to FIG. 5, additional components of the shaft assembly 100 responsible for effecting formation of the surgical clips "C" will be described. The distal portion 124b of the spindle 124 is operatively connected to a jaw cam closure wedge 146 via a slider joint 148. The jaw cam closure wedge 146 is selectively actuatable by the spindle 124 to engage camming features of the pair of jaws 120 to close the pair of jaws 120 and form a surgical clip "C" loaded therewithin. The slider joint 148 supports a latch member 150 for selective engagement with the spindle 124. The latch member 150 may be cammed in a direction toward the spindle 124 during actuation or translation of the spindle 124. In particular, during distal actuation of the spindle 124, at a predetermined distance, the latch member 150 is mechanically forced or cammed into and engaged with a slot in the spindle 124. This engagement of the latch member 150 in the slot of the spindle 124 allows the slider joint 148 to move together with the jaw cam closure wedge 146. The jaw cam closure wedge 146 thus can engage the relevant surfaces of the pair of jaws 120 to close the pair of jaws 120.

The slider joint 148 is connected, at a proximal portion 148a thereof, to a passageway formed in the distal portion 124b of the spindle 124. A distal portion 148b of the slider joint 148 defines a substantially T-shaped profile, wherein the distal portion 148b thereof is connected to the jaw cam closure wedge 146. The latch member 150 functions as a linkage and is disposed to move through an aperture 148c in the slider joint 148 to link with another fixed member and prevent the slider joint 148 from advancing the jaw cam closure wedge 146, and thus preventing the camming of the jaw cam closure wedge 146 from camming the pair of jaws 120 to a closed condition during an initial actuation of a clip applier 10. The distal portion 124b of the spindle 124 is provided with a camming feature configured to move a cam link 152 (pivotably connected to a filler component 154) in a perpendicular manner relative to a longitudinal axis of the spindle 124 during a distal advancement of the spindle 124.

The shaft assembly 100 further includes a clip channel 156 received within the outer tube 122. The clip channel 156 slidably retains the stack of surgical clips "C" therein for application, in seriatim, to the desired tissue or vessel. The clip channel 156 includes a pair of distal stops, such as, for example, resilient tangs 156a, 156b (FIGS. 5 and 7) disposed in parallel relation to one another. The resilient tangs 156a, 156b are transversely spaced from one another a distance substantially equal to a width of the surgical clips "C" so as to capture the distal-most surgical clip "DC" therebetween and resist distal advancement of the distal-most surgical clip "DC." Due to the resilient nature of the resilient tangs 156a, 156b, an application of a threshold distally-oriented force on the distal-most surgical clip "DC" splays outward the resilient tangs 156a, 156b to dislodge the surgical clip "DC" from the hold of the tangs 156a, 156b.

A clip follower 158 is provided and slidably disposed within the clip channel 156 at a location proximal of the stack of surgical clips "C." A spring (not shown) is provided to spring-bias the clip follower 158, and in turn, the stack of surgical clips "C", distally. A clip channel cover 160 is provided that overlies the clip channel 156 to retain and guide the clip follower 158, the spring, and the stack of surgical clips "C" in the clip channel 156.

The shaft assembly 100 further includes a wedge plate 162 that is biased to a proximal position by a wedge plate spring (not shown). The wedge plate 162 is a flat bar shaped member having a number of windows formed therein. The wedge plate 162 has a distal-most position wherein a tip or nose of the wedge plate 162 is inserted between the pair of jaws 120 to maintain the pair of jaws 120 in an open condition for loading of the distal-most surgical clip "DC" therein. The wedge plate 162 has a proximal-most position, maintained by the wedge plate spring, wherein the tip or nose of the wedge plate 162 is retracted from between the pair of jaws 120.

The wedge plate 162 defines a "U" or "C" shaped aperture or notch 162b in a side edge thereof. The C-shaped aperture or notch 162b of the wedge plate 162 selectively engages the cam link 152 supported on the filler plate 154. The cam link 152 selectively engages a surface of C-shaped aperture or notch 162b of the wedge plate 162 to retain the wedge plate 162 in a distal-most position such that a distal tip 162a of the wedge plate 162 is maintained inserted between the pair of jaws 120 to maintain the pair of jaws 120 splayed apart.

The filler component 154 of the shaft assembly 100 is interposed between the clip channel 156 and the wedge plate 162, at a location proximal of the pair of jaws 120. The filler component 154 pivotably supports the cam link 152 that is engagable with the wedge plate 162. During a distal advancement of the spindle 124, a camming feature of the spindle 124 engages a cam link boss of the cam link 152 to thereby move the cam link 152 out of engagement with the wedge plate 162 and permit the wedge plate 162 to return to the proximal-most position as a result of the spring.

It is contemplated that the clip applier 10 may be configured to close, fire, or form surgical clips similar to those shown and described in U.S. Patent Application Publication No. 2017/0128071, and U.S. Pat. Nos. 7,819,886 or 7,905,890, the entire contents of each of which are incorporated herein by reference.

In operation, the clip applier 10 is actuated to effect a stapling function thereof. In particular, the handle assembly 200 (FIGS. 1 and 2) or a control 1004 of a robotic assembly 1000 (FIG. 10) is actuated to advance the spindle 124 of the shaft assembly 100 in a distal direction within and relative to the outer tube 122. During a first distal movement of the spindle 124, the trip block 126 and the associated pusher bar 128 are advanced distally with the spindle 124 due to the preloaded condition of the biasing member 134. As the pusher bar 128 is moved distally, the pusher 144 of the distal portion 128b of the pusher bar 128 carries or pushes the distal-most surgical clip "DC" of the surgical clips "C" through the clip channel 156 in a distal direction until the distal-most clip "DC" is received or captured by the resilient tangs 156a, 156b of the shaft assembly 100. The resilient tangs 156a, 156b resist further distal advancement of the distal-most surgical clip "DC," and in turn the pusher bar 128 and the trip block 126, signifying the conclusion of the first distal movement of the spindle 124, trip block 126, and pusher bar 128.

After completion of the first distal movement of the spindle 124, the spindle 124 undergoes a second distal advancement or movement, via actuation of the handle assembly 200 or the control 1004 (FIG. 10), during which the trip block 126 and pusher bar 128 are resisted from moving therewith due to the engagement of the resilient tangs 156a, 156b with the distal-most surgical clip "DC." As the spindle 124 is distally advanced relative to the trip block 124 and the pusher bar 128, the biasing member 134 is compressed between the proximal wall 134a of the proximal portion 124a of the spindle 124 and the distal wall 136a of the distal portion 126b of the trip block 126 to increase the spring force of the biasing member 134. The trip block 126 and the pusher bar 128 remain axially fixed within the outer tube 122 and relative to the jaws 120 until the spring force of the biasing member 134 exceeds a holding force exerted on the distal-most surgical clip "DC" by the resilient tangs 156a, 156b of the clip channel 156, signifying a completion of the second distal movement of the spindle 124.

Upon the spring force of the biasing member 134 exceeding the holding force of the resilient tangs 156a, 156b of the clip channel 156, the distal-most surgical clip "DC" is forced distally out of the resilient tangs 156a, 156b of the clip channel 156 under the resilient bias of the biasing member 134. Due to the release of the distal-most surgical clip "DC" from the resilient tangs 156a, 156b, the trip block 126 and pusher bar 128 are advanced distally relative to the spindle 124, by the resilient bias of the biasing member 134, to advance the distal-most surgical clip "DC." The pusher bar 128 and trip block 126 are advanced distally relative to the spindle 124 until the distally-oriented wall 136b of the distal portion 126b of the trip block 126 contacts the stop 170 of the shaft assembly 100, whereby the stop 170 resists both the trip block 126 and the pusher bar 128 from advancing further distally. Upon the trip block 126 contacting the stop 170, the pusher 144 of the pusher bar 128 and the associated distal-most surgical clip "DC" are at a location between the jaws 120 and maintained in this location due to the continued distally-oriented bias of the biasing member 134.

With the distal portion 126b of the trip block 126 contacting the stop 170 of the shaft assembly 100, a third distal advancement or movement of the spindle 124 will cease to result in a distal advancement of the trip block 126, the pusher bar 128, and the distal-most surgical clip "DC." The third distal advancement of the spindle 124 approximates the jaws 120 to form the distal-most surgical clip "DC" all while the pusher 144 of the pusher bar 128 remains engaged with the distal-most surgical clip "DC" due to the distally-oriented bias of the biasing member 134. The pusher 144 grasps the backspan of the clip "DC" to maintain the clip "DC" between the jaws 120 as the jaws 120 approximate to form the clip "DC."

To reset the clip applier 10, the spindle 124 is retracted proximally within the outer tube 122 and out of engagement with the jaws 120 to allow the jaws 120 to expand (due to their own spring bias) to their open configuration. Proximal movement of the spindle 124 relative to the trip block 126 and the pusher bar 128 is continued until the distal wall 132b of the proximal portion 124a of the spindle 124 contacts the wall 136b of the distal portion 126b of the trip block 126. As such, a continued proximal retraction of the spindle 124 results in the trip block 126 and the attached pusher bar 128 moving proximally with the spindle 124, thereby removing the pusher 144 of the pusher bar 128 from between the jaws 120.

It is contemplated, and within the scope of the present disclosure, that other endoscopic assemblies, including a pair of jaws having a unique and diverse closure stroke length thereof, may be provided with a drive assembly, similar to any of the drive assemblies described herein, for accommodating and adapting the closure stroke length for the pair of jaws thereof to the constant trigger stroke length.

Accordingly, various endoscopic assemblies, constructed in accordance with the principles of the present disclosure, may be provided which are also capable of firing or forming or closing surgical clips of various sizes, materials, and configurations, across multiple platforms for multiple different manufactures.

Surgical instruments such as the clip appliers described herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Referring to FIG. 10, a medical work station is shown generally as robotic system or work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, the shaft assembly of FIGS. 1-9, in accordance with any one of several embodiments disclosed herein, as will be described in greater detail below.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the shaft assembly 100, execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of the shaft assembly 100. Medical work station 1000 may also include more than two robot arms 1002, 1003, the additional robot arms likewise being connected to control device 1004 and being telemanipulatable by means of operating console 1005. A surgical end effector, such as, for example, the shaft assembly 100 of the clip applier 10 (FIGS. 1-9), may also be attached to the additional robot arm. Medical work station 1000 may include a database 1014, in particular coupled to with control device 1004, in which are stored, for example, pre-operative data from patient/living being 1013 and/or anatomical atlases.

Reference is made herein to U.S. Pat. No. 8,828,023, the entire content of which is incorporated herein by reference, for a more detailed description of the construction and operation of an exemplary robotic surgical system.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An apparatus for application of surgical clips to body tissue, the apparatus comprising:
   a handle assembly; and
   a shaft assembly selectively connectable to the handle assembly and actuatable upon actuation of the handle assembly, the shaft assembly including:
      a pair of jaws movable between a spaced-apart position and an approximated position;
      an elongated spindle having a proximal portion configured to be coupled to an actuator, and a distal portion operably coupled to the pair of jaws to selectively approximate the pair of jaws during distal advancement of the spindle;
      a trip block reciprocally supported on the proximal portion of the spindle and axially movable both with and relative to the spindle;
      a biasing member extending between the proximal portion of the spindle and the trip block; and
      a pusher bar having a proximal portion fixedly coupled to the trip block, and a distal portion configured to load a distal-most surgical clip into the pair of jaws during distal movement of the trip block, via distal movement of the spindle, and remain in a distally advanced position during approximation of the pair of jaws; and
   wherein both the trip block and the pusher bar are configured to move with the spindle in response to a first distal movement of the spindle to engage the distal portion of the pusher bar with the distal-most surgical clip, and movement of both the trip block and the pusher bar with the spindle is resisted during a second distal movement of the spindle.

2. The apparatus according to claim 1, wherein the shaft assembly further includes a clip channel slidably retaining a stack of surgical clips including the distal-most surgical clip therein, the clip channel having a distal stop that couples to the distal portion of the pusher bar via the distal-most surgical clip after the first distal movement of the spindle, whereby the distal stop resists both the trip block and the pusher bar from advancing distally during the second distal movement of the spindle.

3. The apparatus according to claim 2, wherein the second distal movement of the spindle compresses the biasing member between the spindle and the trip block to increase a spring force of the biasing member.

4. The apparatus according to claim 3, wherein the spring force of the biasing member exceeds a holding force exerted on the distal-most surgical clip by the distal stop of the clip channel upon the spindle completing the second distal movement, such that the trip block and the pusher bar are moved distally relative to the spindle via the biasing member to position the distal-most surgical clip between the pair of jaws.

5. The apparatus according to claim 4, wherein the pair of jaws are configured to form the distal-most surgical clip in response to a third distal movement of the spindle while the distal portion of the pusher bar is maintained in engagement with the distal-most surgical clip by the biasing member.

6. The apparatus according to claim 2, wherein the distal stop of the clip channel includes at least one resilient tang that captures the distal-most clip to resist distal movement of the distal-most surgical clip relative thereto.

7. The apparatus according to claim 1, wherein the biasing member is in a preloaded condition prior to the first distal movement of the spindle to distally bias the trip block and the pusher bar relative to the spindle.

8. The apparatus according to claim 1, wherein the proximal portion of the spindle defines an elongate channel, and the trip block defines an elongate channel in communication with the elongate channel of the spindle, the elongate channel of each of the spindle and the trip block having the biasing member extending therethrough.

9. The apparatus according to claim 8, wherein the proximal portion of the spindle has a distally-oriented wall having a proximal portion of the biasing member coupled thereto, and the trip block has a proximally-oriented wall having a distal portion of the biasing member coupled thereto.

10. The apparatus according to claim 8, wherein the pusher bar includes a fin extending laterally from the proximal portion thereof, and the trip block defines a notch having the fin of the pusher bar received therein.

11. The apparatus according to claim 1, wherein the shaft assembly includes a stop axially fixed relative to the pair of jaws, the trip block having a distal portion configured to contact the stop upon the trip block moving to a distal position, such that the stop resists further distal movement of the pusher bar.

12. The apparatus according to claim 11, wherein the distal portion of the pusher bar positions the distal-most surgical clip between the pair of jaws when the trip block is in the distal position.

13. The apparatus according to claim 11, wherein the shaft assembly includes an outer member having the stop axially fixed therein.

14. The apparatus according to claim 1, wherein the spindle defines a longitudinally-extending channel through which a distal portion of the trip block axially moves, the channel of the spindle having a distal limit that contacts the distal portion of the trip block during proximal retraction of the spindle.

15. The apparatus according to claim 1, wherein the pusher bar includes a pusher formed at a distal end thereof, wherein the pusher has a narrow profile for allowing the pair of jaws to move to the approximated position while the pusher is disposed therebetween.

16. A shaft assembly of an apparatus for applying surgical clips to body tissue, the shaft assembly comprising:
  a pair of jaws movable between a spaced-apart position and an approximated position;
  an elongated spindle having a proximal portion configured to be coupled to an actuator, and a distal portion configured to be operably coupled to the pair of jaws to selectively approximate the pair of jaws during distal advancement of the spindle;
  a trip block reciprocally supported on the proximal portion of the spindle and axially movable both with and relative to the spindle;
  a biasing member extending between the proximal portion of the spindle and the trip block;
  a pusher bar having a proximal portion fixedly coupled to the trip block, and a distal portion configured to load a distal-most surgical clip into the pair of jaws during distal movement of the trip block, via distal movement of the spindle, and remain in a distally advanced position during approximation of the pair of jaws; and
  wherein both the trip block and the pusher bar are configured to move with the spindle in response to a first distal movement of the spindle to engage the distal portion of the pusher bar with the distal-most surgical clip, and movement of both the trip block and the pusher bar with the spindle is resisted during a second distal movement of the spindle.

17. The shaft assembly according to claim 16, further comprising a clip channel slidably retaining a stack of surgical clips including the distal-most surgical clip therein, the clip channel having a distal stop that couples to the distal portion of the pusher bar via the distal-most surgical clip after the first distal movement of the spindle, whereby the distal stop resists both the trip block and the pusher bar from advancing distally during the second distal movement of the spindle.

18. The shaft assembly according to claim 17, wherein the second distal movement of the spindle compresses the biasing member between the spindle and the trip block to increase a spring force of the biasing member.

19. The shaft assembly according to claim 18, wherein the spring force of the biasing member exceeds a holding force exerted on the distal-most surgical clip by the distal stop of the clip channel upon the spindle completing the second distal movement, such that the pusher bar is moved distally relative to the spindle via the biasing member to position the distal-most surgical clip between the pair of jaws.

* * * * *